US007740637B2

(12) United States Patent
Gandhi et al.

(10) Patent No.: US 7,740,637 B2
(45) Date of Patent: *Jun. 22, 2010

(54) APPARATUS AND METHOD FOR DEPLOYMENT OF A THERAPEUTIC DEVICE USING A CATHETER

(75) Inventors: Deepak Gandhi, Huntington Beach, CA (US); Kamal Ramzipoor, Fremont, CA (US); Henry N. Padilla, Temecula, CA (US)

(73) Assignee: Micrus Endovascular Corporation, San Jose, CA (US)

( * ) Notice: Subject to any disclaimer, the term of this patent is extended or adjusted under 35 U.S.C. 154(b) by 9 days.

This patent is subject to a terminal disclaimer.

(21) Appl. No.: 11/726,074

(22) Filed: Mar. 21, 2007

(65) Prior Publication Data
US 2007/0167911 A1    Jul. 19, 2007

Related U.S. Application Data

(63) Continuation-in-part of application No. 11/020,936, filed on Dec. 22, 2004, now Pat. No. 7,198,613, which is a continuation of application No. 10/290,777, filed on Nov. 7, 2002, now Pat. No. 6,966,892, which is a continuation of application No. 09/501,466, filed on Feb. 9, 2000, now Pat. No. 6,478,773.

(51) Int. Cl.
*A61F 11/00* (2006.01)
*A61F 7/12* (2006.01)
*A61M 29/00* (2006.01)

(52) U.S. Cl. .................. 606/108; 606/200; 604/144

(58) Field of Classification Search .................. 604/113, 604/114, 93.01, 95.05, 533, 531; 606/108, 606/191, 192, 194, 195, 198, 200, 32; 623/1.23, 623/1.11, 1.12, 1.19
See application file for complete search history.

(56) References Cited

U.S. PATENT DOCUMENTS

| 1,341,052 A | 5/1920 | Gale |
| 2,078,182 A | 4/1937 | MacFarland |
| 2,549,335 A | 4/1951 | Rahthus |
| 3,334,629 A | 8/1967 | Cohn |

(Continued)

FOREIGN PATENT DOCUMENTS

DE    4102550 A1    8/1991

(Continued)

OTHER PUBLICATIONS

US 5,766,161, 7/1998, Gloverman (withdrawn).

(Continued)

*Primary Examiner*—Kevin C Sirmons
*Assistant Examiner*—Catherine N Witczak
(74) *Attorney, Agent, or Firm*—Fulwider Patton LLP

(57) ABSTRACT

The apparatus for deployment of an intravascular therapeutic device, includes an elongated, flexible pusher member and a therapeutic device connected to a severable portion of a first connector member mounted to the flexible pusher member with an elongated second connector member connected to the therapeutic device. The first connector member or second connector member may be capable of being broken by heat, and a heat source is provided for heating and breaking the first connector member or the second connector member to release the therapeutic device.

22 Claims, 3 Drawing Sheets

U.S. PATENT DOCUMENTS

| | | |
|---|---|---|
| 3,485,234 A | 12/1969 | Stevens |
| 3,649,224 A | 3/1972 | Anderson et al. |
| 3,868,956 A | 3/1975 | Alfidi et al. |
| 4,327,734 A | 5/1982 | White, Jr. |
| 4,341,218 A | 7/1982 | U |
| 4,346,712 A | 8/1982 | Handa et al. |
| 4,402,319 A | 9/1983 | Handa et al. |
| 4,441,495 A | 4/1984 | Hicswa |
| 4,494,531 A | 1/1985 | Gianturco |
| 4,512,338 A | 4/1985 | Balko et al. |
| 4,545,367 A | 10/1985 | Tucci |
| 4,553,545 A | 11/1985 | Maass et al. |
| 4,611,594 A | 9/1986 | Grayhack et al. |
| 4,629,458 A | 12/1986 | Pinchuk |
| 4,638,803 A | 1/1987 | Rand |
| RE32,348 E | 2/1987 | Pevsner |
| 4,655,771 A | 4/1987 | Wallsten |
| 4,662,068 A | 5/1987 | Polonsky |
| 4,670,286 A | 6/1987 | Nyilas et al. |
| 4,718,907 A | 1/1988 | Karwoski et al. |
| 4,732,152 A | 3/1988 | Wallsten et al. |
| 4,748,986 A | 6/1988 | Morrison et al. |
| 4,768,507 A | 9/1988 | Fishell et al. |
| 4,795,458 A | 1/1989 | Regan |
| 4,798,606 A | 1/1989 | Pinchuk |
| 4,800,882 A | 1/1989 | Gianturco |
| 4,813,925 A | 3/1989 | Anderson, Jr. et al. |
| 4,820,298 A | 4/1989 | Leveen et al. |
| 4,830,003 A | 5/1989 | Wolff et al. |
| 4,850,960 A | 7/1989 | Grayzel |
| 4,856,516 A | 8/1989 | Hillstead |
| 4,873,978 A | 10/1989 | Ginsburg |
| 4,950,258 A | 8/1990 | Kawai et al. |
| 4,954,126 A | 9/1990 | Wallsten |
| 4,957,479 A | 9/1990 | Roemer |
| 4,957,501 A | 9/1990 | Lahille et al. |
| 4,990,155 A | 2/1991 | Wilkoff |
| 4,994,069 A | 2/1991 | Ritchart et al. |
| 4,994,071 A | 2/1991 | MacGregor |
| 5,002,556 A | 3/1991 | Ishida et al. |
| 5,015,253 A | 5/1991 | MacGregor |
| 5,019,090 A | 5/1991 | Pinchuk |
| 5,026,377 A | 6/1991 | Burton et al. |
| 5,035,706 A | 7/1991 | Giantureo et al. |
| 5,037,377 A | 8/1991 | Alonso |
| 5,041,084 A | 8/1991 | DeVries et al. |
| 5,041,126 A | 8/1991 | Gianturco |
| 5,061,275 A | 10/1991 | Wallsten et al. |
| 5,064,435 A | 11/1991 | Porter |
| 5,071,407 A | 12/1991 | Termin et al. |
| 5,101,094 A | 3/1992 | Keller et al. |
| 5,104,404 A | 4/1992 | Wolff |
| 5,108,407 A | 4/1992 | Geremia et al. |
| 5,109,867 A | 5/1992 | Twyford, Jr. |
| 5,122,136 A | 6/1992 | Guglielmi et al. |
| 5,133,364 A | 7/1992 | Palermo et al. |
| 5,133,731 A | 7/1992 | Butler et al. |
| 5,133,732 A | 7/1992 | Wiktor |
| 5,141,502 A | 8/1992 | Macaluso, Jr. |
| 5,143,085 A | 9/1992 | Wilson |
| 5,147,370 A | 9/1992 | McNamara et al. |
| 5,151,105 A | 9/1992 | Kwan-Gett |
| 5,152,784 A | 10/1992 | Tsilibary |
| 5,160,341 A | 11/1992 | Brenneman et al. |
| 5,171,273 A | 12/1992 | Silver et al. |
| 5,176,625 A | 1/1993 | Brisson |
| 5,176,661 A | 1/1993 | Evard et al. |
| 5,181,921 A | 1/1993 | Makita et al. |
| 5,183,085 A | 2/1993 | Timmermans |
| 5,186,992 A | 2/1993 | Kite, III |
| 5,188,621 A | 2/1993 | Samson |
| 5,192,290 A | 3/1993 | Hilal |
| 5,197,977 A | 3/1993 | Hoffman, Jr. et al. |
| 5,203,772 A | 4/1993 | Hammerslag et al. |
| 5,211,658 A | 5/1993 | Clouse |
| 5,217,484 A | 6/1993 | Marks |
| 5,222,969 A | 6/1993 | Gillis |
| 5,222,970 A | 6/1993 | Reeves |
| 5,224,953 A | 7/1993 | Morgentaler |
| 5,226,911 A | 7/1993 | Chee et al. |
| 5,226,913 A | 7/1993 | Pinchuk |
| 5,228,453 A | 7/1993 | Sepetka |
| 5,234,437 A | 8/1993 | Sepetka |
| 5,234,456 A | 8/1993 | Silvestrini |
| 5,238,004 A | 8/1993 | Sahatjian et al. |
| 5,250,071 A | 10/1993 | Palermo |
| 5,256,146 A | 10/1993 | Ensminger et al. |
| 5,258,042 A | 11/1993 | Mehta |
| 5,261,916 A | 11/1993 | Engelson |
| 5,275,173 A | 1/1994 | Samson et al. |
| 5,304,194 A | 4/1994 | Chee et al. |
| 5,312,415 A | 5/1994 | Palermo |
| 5,314,472 A | 5/1994 | Fontaine |
| 5,322,501 A | 6/1994 | Mahmud-Durrani |
| 5,334,217 A | 8/1994 | Das |
| 5,336,205 A | 8/1994 | Zenzen et al. |
| 5,341,818 A | 8/1994 | Abrams et al. |
| 5,342,387 A | 8/1994 | Summers |
| 5,350,397 A | 9/1994 | Palermo et al. |
| 5,354,295 A | 10/1994 | Guglielmi et al. |
| 5,354,309 A | 10/1994 | Schnepp-Pesch et al. |
| 5,368,049 A | 11/1994 | Raman et al. |
| 5,373,856 A | 12/1994 | Grenouillet |
| 5,382,259 A | 1/1995 | Phelps et al. |
| 5,383,887 A | 1/1995 | Nadal |
| 5,395,390 A | 3/1995 | Simon et al. |
| 5,405,377 A | 4/1995 | Cragg |
| 5,409,015 A | 4/1995 | Palermo |
| 5,411,475 A | 5/1995 | Atala et al. |
| 5,413,597 A | 5/1995 | Krajicek |
| 5,415,664 A | 5/1995 | Pinchuk |
| 5,417,708 A | 5/1995 | Hall et al. |
| 5,423,829 A | 6/1995 | Pham et al. |
| 5,433,723 A | 7/1995 | Lindenberg et al. |
| 5,441,516 A | 8/1995 | Wang et al. |
| 5,443,478 A | 8/1995 | Purdy |
| 5,443,498 A | 8/1995 | Fontaine |
| 5,484,449 A | 1/1996 | Amundson et al. |
| 5,500,013 A | 3/1996 | Buscemi et al. |
| 5,514,115 A | 5/1996 | Frantzen et al. |
| 5,514,176 A | 5/1996 | Bosley, Jr. |
| 5,520,194 A | 5/1996 | Miyata et al. |
| 5,522,822 A | 6/1996 | Phelps et al. |
| 5,522,836 A | 6/1996 | Palermo |
| 5,523,092 A | 6/1996 | Hanson et al. |
| 5,527,336 A | 6/1996 | Rosenbluth et al. |
| 5,540,701 A | 7/1996 | Sharkey et al. |
| 5,549,624 A | 8/1996 | Mirigian et al. |
| 5,562,641 A | 10/1996 | Flomenblit et al. |
| 5,562,698 A | 10/1996 | Parker |
| 5,569,245 A | 10/1996 | Guglielmi et al. |
| 5,578,074 A | 11/1996 | Mirigian |
| 5,582,619 A | 12/1996 | Ken |
| 5,603,694 A | 2/1997 | Brown et al. |
| 5,607,445 A | 3/1997 | Summers |
| 5,609,627 A | 3/1997 | Goicoechea et al. |
| 5,613,981 A | 3/1997 | Boyle et al. |
| 5,624,461 A | 4/1997 | Mariant |
| 5,637,113 A | 6/1997 | Tartaglia et al. |
| 5,638,827 A | 6/1997 | Palmer et al. |
| 5,639,277 A | 6/1997 | Mariant et al. |
| 5,643,254 A | 7/1997 | Scheldrup et al. |
| 5,643,339 A | 7/1997 | Kavteladze et al. |
| 5,645,564 A | 7/1997 | Northrup et al. |

| | | | |
|---|---|---|---|
| 5,649,949 A | 7/1997 | Wallace et al. |
| 5,653,726 A | 8/1997 | Kieturakis |
| 5,653,727 A | 8/1997 | Wiktor |
| 5,666,968 A | 9/1997 | Imran et al. |
| 5,667,522 A | 9/1997 | Flomenblit et al. |
| 5,676,697 A | 10/1997 | McDonald |
| 5,690,643 A | 11/1997 | Wijay |
| 5,690,666 A | 11/1997 | Berenstein et al. |
| 5,690,671 A | 11/1997 | McGurk et al. |
| 5,693,085 A | 12/1997 | Buirge et al. |
| 5,702,373 A | 12/1997 | Samson |
| 5,702,414 A | 12/1997 | Richter et al. |
| 5,713,907 A | 2/1998 | Hogendijk et al. |
| 5,722,989 A | 3/1998 | Fitch et al. |
| 5,725,546 A | 3/1998 | Samson |
| 5,733,329 A | 3/1998 | Wallace et al. |
| 5,743,905 A | 4/1998 | Eder et al. |
| 5,746,765 A | 5/1998 | Kleshinski et al. |
| 5,746,769 A | 5/1998 | Ton et al. |
| 5,749,883 A | 5/1998 | Halpern |
| 5,749,891 A | 5/1998 | Ken et al. |
| 5,749,894 A | 5/1998 | Engelson |
| 5,749,918 A | 5/1998 | Hogendijk et al. |
| 5,749,921 A | 5/1998 | Lenker et al. |
| 5,759,161 A | 6/1998 | Ogawa et al. |
| 5,788,653 A | 8/1998 | Lorenzo |
| 5,797,957 A | 8/1998 | Palmer et al. |
| 5,800,455 A | 9/1998 | Palermo |
| 5,800,526 A | 9/1998 | Anderson et al. |
| 5,814,062 A | 9/1998 | Sepetka et al. |
| 5,824,059 A | 10/1998 | Wijay |
| 5,911,737 A | 6/1999 | Lee et al. |
| 5,944,733 A | 8/1999 | Engelson |
| 5,947,963 A | 9/1999 | Guglielmi |
| 5,964,771 A | 10/1999 | Beyar et al. |
| 5,984,929 A | 11/1999 | Bashiri et al. |
| 5,989,242 A | 11/1999 | Saadat et al. |
| 6,059,815 A | 5/2000 | Lee et al. |
| 6,102,933 A | 8/2000 | Lee et al. |
| 6,159,165 A | 12/2000 | Ferrera et al. |
| 6,168,570 B1 | 1/2001 | Ferrera |
| 6,224,610 B1 | 5/2001 | Ferrera |
| 6,270,495 B1 | 8/2001 | Palermo |
| 6,296,622 B1 | 10/2001 | Debeer |
| 6,478,773 B1 * | 11/2002 | Gandhi et al. | 604/113 |
| 6,500,149 B2 * | 12/2002 | Gandhi et al. | 604/113 |
| 6,616,617 B1 | 9/2003 | Ferrera et al. |
| 6,656,173 B1 | 12/2003 | Palermo |
| 6,966,892 B2 * | 11/2005 | Gandhi et al. | 604/114 |
| 7,198,613 B2 * | 4/2007 | Gandhi et al. | 604/114 |
| 7,575,582 B2 | 8/2009 | Gandhi et al. |
| 7,578,826 B2 | 8/2009 | Gandhi et al. |
| 2002/0138025 A1 | 9/2002 | Gellman et al. |
| 2005/0043755 A1 | 2/2005 | Wilson et al. |
| 2006/0020333 A1 | 1/2006 | Lashinski |
| 2006/0025801 A1 | 2/2006 | Lulo et al. |
| 2006/0265001 A1 | 11/2006 | Marks |
| 2007/0060938 A1 | 3/2007 | Dziadik |

FOREIGN PATENT DOCUMENTS

| | | |
|---|---|---|
| DE | 19704269 A1 | 11/1997 |
| EP | 0 183 372 A1 | 6/1986 |
| EP | 0 278 937 | 8/1988 |
| EP | 0 382 014 A1 | 8/1990 |
| EP | 0 518 704 A1 | 12/1992 |
| EP | 0 627 201 A1 | 12/1994 |
| FR | 592.182 | 7/1925 |
| GB | 2 066 839 A | 7/1981 |
| WO | WO 92/14408 | 3/1992 |
| WO | WO 94/16629 | 4/1994 |
| WO | WO 95/18585 | 7/1995 |
| WO | WO 95/21592 | 8/1995 |
| WO | WO 97/48351 | 12/1997 |
| WO | 2006076537 A | 7/2006 |

OTHER PUBLICATIONS

Christos A. Athanasoulis, M.D., The New England Journal of Medicine, May 15, 1980, "Therapeutic Applications of Angiography" pp. 1117-1125 (1 of 2).

Christos A. Athanasoulis, M.D., The New England Journal of Medicine, May 22, 1980, "Therapeutic Applications of Angiography" pp. 1174-1179 (2 of 2).

Alex Berenstein, M.D. and Irvin I. Kricheff, M.D., "Catheter and Material Selection for Transarterial Embolization: Technical Considerations" Radiology, Sep. 1979; pp. 631-639.

O.A. Battista, et al. Journal of Applied Polymer Science 1967 "Colloidal Macromolecular Phenomena. Part II. Novel Microcrystals of Polymers" pp. 481-498.

Sadek K. Hilal, M.D. et al. Journal of Neurological Surgery "Therapeutic Percutaneous Embolization for Extra-Axial Vascular Lesions of the Head, Neck and Spine" Sep. 1975; pp. 275-287.

Stephen L. Kaufman, M.D. et al. Investigative Radiology, May-Jun. 1978, "Transcatheter Embolization with Microfibrillar Collagen in Swine"; pp. 200-204.

Ashok J. Kumar, et al., Journal of Neuroradiology (1982) "Preoperative Embolization of Hypervascular Head and Neck Neoplasms Using Microfibrillar Collagen", pp. 163-168.

Richard E. Latchaw, M.D. et al., Radiology (1979) "Polyvinyl Foam Embolization of Vascular and Neoplastic Lesions of the Head, Neck and Spine" pp. 669-679.

Stewart R. Reuter, M.D. et al. American Journal of Radiology, Sep. 1975, "Selective Arterial Embolization For Control of Massive Upper Gastrointestinal Bleeding" pp. 119-126.

Glenn H. Roberson, et al., American Journal of Radiology, Oct. 1979, "Therapeutic Embolization of Juvenile Angiofibroma" pp. 657-663.

Sidney Wallace, M.D. et al., Cancer, Oct. 1979, "Arterial Occlusion of Pelvic Bone Tumors"; pp. 322-325 & 661-663.

"Mechanical Devices for Arterial Occlusion" By C. Giantgurco, M.D., et al., Jul. 1975, pp. 428-435.

"Therapeutic Vascular Occlusion Utilizing Steel Coil Technique: Clinical Applications" By Sidney Wallace, et al., Am J. Roentgenol (1976); pp. 381-387.

"Transcatheter Intravascular Coil Occlusion of Experimental Arteriovenous Fistulas", By James H. Anderson, et al., Am. J. Roentgenol, Nov. 1977, pp. 795-798.

"'Mini' Gianturco Stainless Steel Coils For Transcatheter Vascular Occusion" By James H. Anderson, et al., From The Department of Diagnostic Radiology at the University of Texas System Cancer Center, Aug. 1977, pp. 301-303.

"A new Improved Coil For Tapered-Tip Catheter For Arterial Occlusion" By Vincent P. Chuang, M.D., et al., May 1980, pp. 507-509.

"Retrievable Gianturco-Coil Introducer" By Jeffrey Hawkins, et al., From the Department of Radiology at the University of Florida Medical Center and Hawk Prototype Equipment 1986.

International Search Report issued Mar. 25, 2009, pp. 1-7.

\* cited by examiner

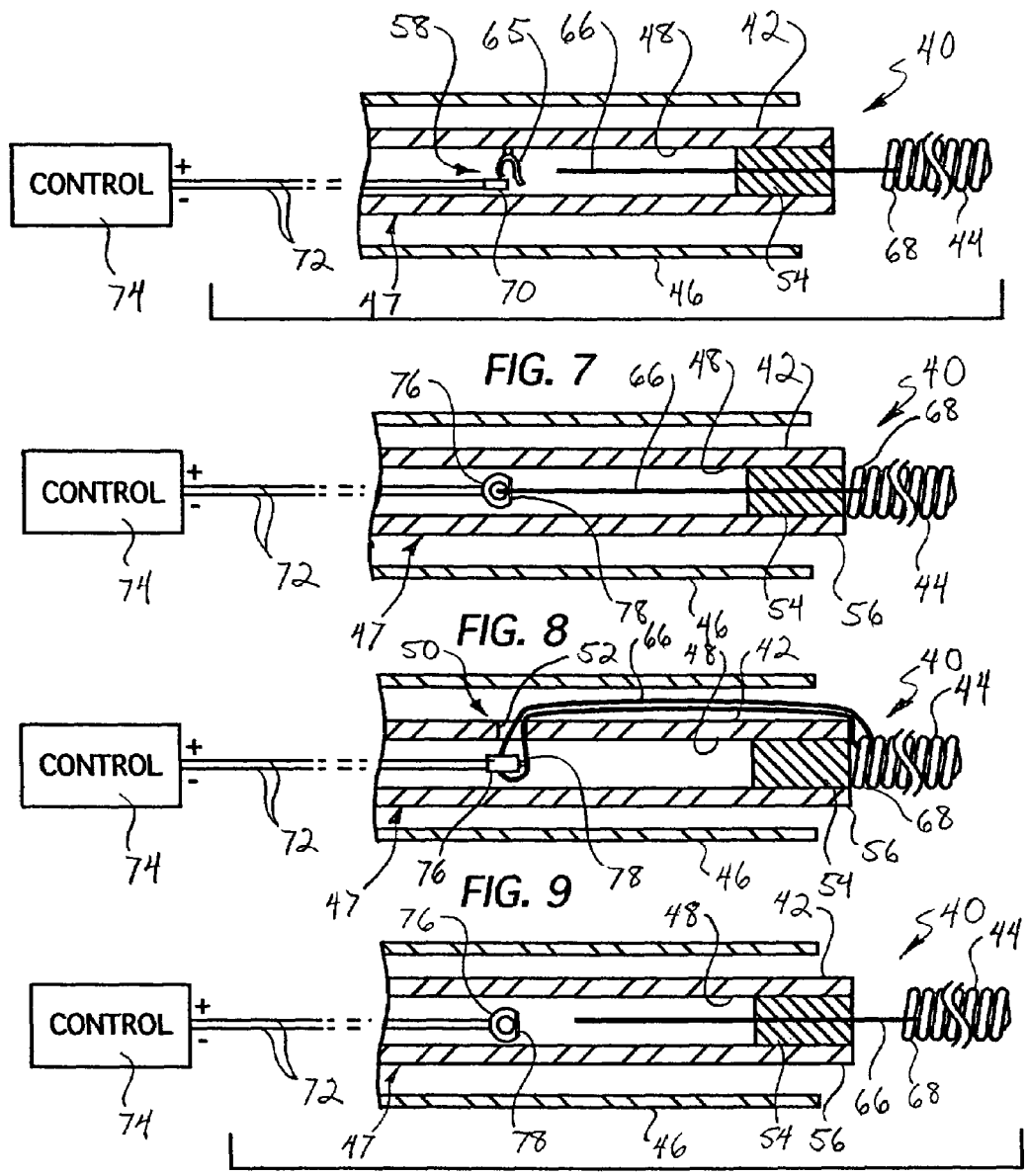

APPARATUS AND METHOD FOR DEPLOYMENT OF A THERAPEUTIC DEVICE USING A CATHETER

CROSS REFERENCES TO RELATED APPLICATIONS

This is a continuation-in-part of application Ser. No. 11/020,936, filed 22 Dec. 2004, now U.S. Pat. No. 7,198,613, which is a continuation of application Ser. No. 10/290,777, filed 7 Nov. 2002, now U.S. Pat. No. 6,966,892, which is a continuation of application Ser. No. 09/501,466, filed 9 Feb. 2000, now U.S. Pat. No. 6,478,773.

FIELD OF THE INVENTION

This invention relates generally to devices for intravascular interventional therapeutic treatment or vascular surgery for treatment of defects in the vasculature, and more particularly concerns a system and method for delivering intravascular interventional devices, such as for treatment of aneurysms.

BACKGROUND OF THE INVENTION

Vascular interventional devices such as vasoocclusive devices are typically placed within the vasculature of the human body by use of a catheter. Vascular interventional devices such as stents can be placed within an occluded vessel to facilitate blood flow through the vessel, and vasoocclusive devices are typically either placed within a blood vessel to block the flow of blood through the vessel by forming an embolus, or are placed within an aneurysm stemming from the vessel to form an embolus within the aneurysm. Stents can have a wide variety of configurations, but generally need to be placed and then released at a desired location within a blood vessel. Vasoocclusive devices used for these procedures can also have a wide variety of configurations, and aneurysms have been treated with external surgically placed clips, detachable vasoocclusive balloons and embolus generating vasoocclusive devices such as one or more vasoocclusive coils.

The delivery of such vasoocclusive devices have typically been accomplished by a variety of means, including via a catheter in which the device is pushed through an opening at the distal end of the catheter by a pusher to deploy the device. The vasoocclusive devices can be produced in such a way that they will pass through the lumen of a catheter in a linear shape and take on a complex shape as originally formed after being deployed into the area to be treated, such as an aneurysm.

One conventional releasable balloon catheter used to embolize vascular lesions has a tube portion made of a material such as a hydrophilic polymer, located between the catheter and the balloon, that can be melted by heating the tube, or can be dissolved in the blood when heated, and electrodes are provided for heating the tube. Another conventional technique for separating a balloon from a balloon catheter involves the melting and breaking of a connecting member between the balloon and the catheter body, when power is supplied to electrodes provided for heating the connecting member. When the connecting member is heated to temperatures of about 70° C. and slight tension is applied, the balloon can be separated from the main catheter body.

An implant delivery assembly is also known that is used for delivery of implants such as embolic coils, utilizing a shape memory decoupling mechanism activated when exposed to body temperature. A cooling solution is flushed through the catheter during introduction and placement of the implant in order to prevent premature release of the implant prior to the time that the implant is to be released. Another implant delivery assembly includes an electrical heating system for heating the coupling mechanism to a temperature at which the shape memory material returns to its original shape, to deploy the implant.

Another device is known in which a device to be implanted is detached by application of a high-frequency current which melts and severs a resin that is used to retain the device to be implanted until the device is to be deployed. In another known device, an electrolytically severable link is dissolved by activation of a power source electrically coupled to the electrolytically severable link to detach the device to be implanted.

In another conventional technique, a conductive guidewire delivers a high frequency current through the guidewire to melt and sever a joint to detach an implanted device from the guidewire. The patient is grounded during the procedure, and current is introduced via the guidewire, rather than with a two way current path.

Such devices that release the interventional device by melting or dissolving the intermediate section between the catheter tip and implanted device may cause thermal damage of surrounding tissues during detachment that can cause embolization in the bloodstream, and may also potentially release undesirable particles of materials into the bloodstream that can also cause embolization in the bloodstream. There is therefore a need for a precise method of deploying therapeutic interventional devices without compromising the position of the implant, without causing thermal damage to surrounding tissues, and without releasing undesirable particles of materials into the bloodstream and risking the formation of emboli in the bloodstream. The present invention meets these and other needs.

SUMMARY OF THE INVENTION

Briefly, and in general terms, the present invention provides for an apparatus for deployment of an intravascular therapeutic device, such as a vasoocclusive device, a microcoil, at least one electrode, a stent, or a coated coil, for example, using an elongated, flexible pusher member. The therapeutic device is connected to a first connector member mounted to the flexible pusher member with an elongated second connector member connected between the first connector member and the therapeutic device. At least one of the first and second connector members includes a severable portion that is capable of being severed, such as by melting or degradation, by heat. A heat source is provided for heating and breaking the severable portion of the first or second connector member to release the therapeutic device. The first connector member may be formed from a molded thermoplastic material, such as high density polyethylene, and the elongated second connector member may be a connector fiber, or a ribbon, for example. The elongated second connector member may also be formed from a thermoplastic material, such as high density polyethylene. The heat source is advantageously contained substantially within the pusher member, which provides a sufficient amount of thermal insulation to eliminate the potential for thermal damage to surrounding tissues during detachment of the therapeutic device. Since the severable first connecting member is heated and broken at a location fully contained within the pusher member, the potential for releasing undesirable particles of materials into the bloodstream and consequent embolization in the bloodstream is virtually eliminated.

The invention accordingly provides for an apparatus for release and deployment of a therapeutic device within the vasculature of a patient, the apparatus including an elongated, flexible pusher member having an interior lumen, a first connector member mounted to the elongated, flexible pusher member. In one aspect, the first connector member may have a severable portion capable of being broken by heating disposed within the elongated, flexible pusher member. An elongated second connector member is connected to the therapeutic device and detachably connected to the first connector member. The elongated second connector member thereby connects the therapeutic device to the pusher member for placement of the therapeutic device within the vasculature, and in one aspect, the elongated second connector member may have a severable portion capable of being broken by heating disposed within the elongated, flexible pusher member.

In one aspect, a heat source may be disposed in the interior lumen of the pusher member adjacent to the first connector member for heating the severable portion of the first connector member to cause the severable portion of the first connector member to break and release the elongated second connector member for detaching and deploying the therapeutic device from the flexible pusher member when a desired placement of the therapeutic device within the vasculature is achieved.

In another aspect, the first connector member may be formed from a molded thermoplastic, such as high density polyethylene, for example. The first connector member may be molded in the form of a rod extending across the interior diameter of the interior lumen of the pusher member, a post, a ring, or other similar suitable configurations. In another aspect, the heat source may include an electrical resistance heat source coil. Alternatively, the heat source may include an induction ring, and may be included in the first connector member, for severing the elongated second connector member. A control unit is typically connected to the heat source to supply electrical current to the heat source. The flexible pusher member typically includes a heat insulating shaft having an entry port communicating with the interior lumen of the pusher member, and the heat source is disposed in the interior lumen of the pusher member adjacent to the entry port. The flexible pusher member has a distal tip, and in one aspect, the heat source may be spaced apart from the distal tip of the flexible pusher member.

In other aspects, the elongated second connector member may be a connector fiber, or may be a ribbon. The therapeutic device may be a vasoocclusive device, a microcoil, at least one electrode, a stent, or a coated coil, for example.

These and other aspects and advantages of the invention will become apparent from the following detailed description and the accompanying drawings, which illustrate by way of example the features of the invention.

BRIEF DESCRIPTION OF THE DRAWINGS

FIG. 7 is a side sectional view of the apparatus of FIG. 4, illustrating release of the therapeutic device.

FIG. 8 is a top sectional view of a fourth embodiment of the apparatus for release and deployment of a therapeutic device.

FIG. 9 is a side sectional view of the apparatus of FIG. 8.

FIG. 10 is a side sectional view of the apparatus of FIG. 8, illustrating release of the therapeutic device.

DETAILED DESCRIPTION OF THE INVENTION

Figure 1:
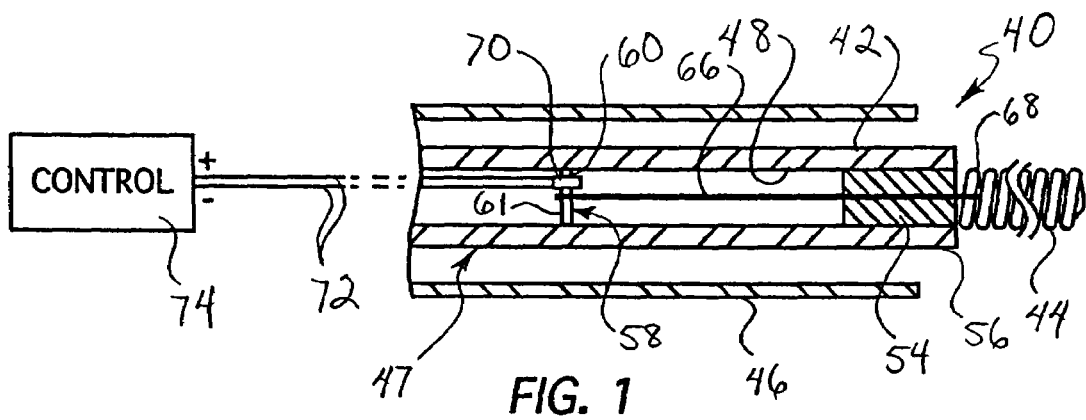
FIG. 1 is a top sectional view of a first embodiment of the apparatus for release and deployment of a therapeutic device.

While vasoocclusive devices have conventionally been delivered to a portion of a patient's vasculature to be treated through a delivery catheter by means of a pusher device, such conventional methods can involve separation of the vasoocclusive device from the pusher device in ways that result in injury to the vasculature, such as by causing thermal damage of surrounding tissues during detachment that can cause embolization in the bloodstream, or by release of undesirable particles of materials into the bloodstream that can cause embolization in the bloodstream.

With reference to FIGS. 1-10, the invention provides for an apparatus 40 including an elongated, flexible pusher member 42 for release and deployment of a therapeutic device 44 such as a vasoocclusive device, which may for example be a microcoil, only a portion of which is shown, within the vasculature of a patient, through a delivery catheter 46. The therapeutic device may alternatively be one or more electrodes, a stent, a coated coil, or the like, for example. The pusher member has a shaft 47 that provides a measure of thermal insulation to an interior lumen 48, as will be further explained below. The shaft of the pusher member typically has an outer diameter of approximately 0.015", and an inside diameter of approximately 0.007, and can be formed from polyethylene terephthalate (PET) tubing.

Figure 2:
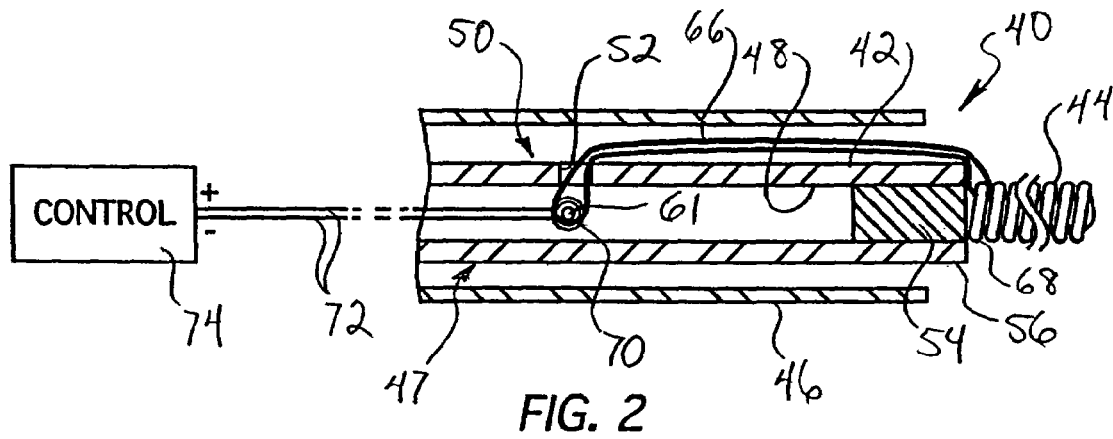
FIG. 2 is a side sectional view of the apparatus of FIG. 1.
Figure 5:
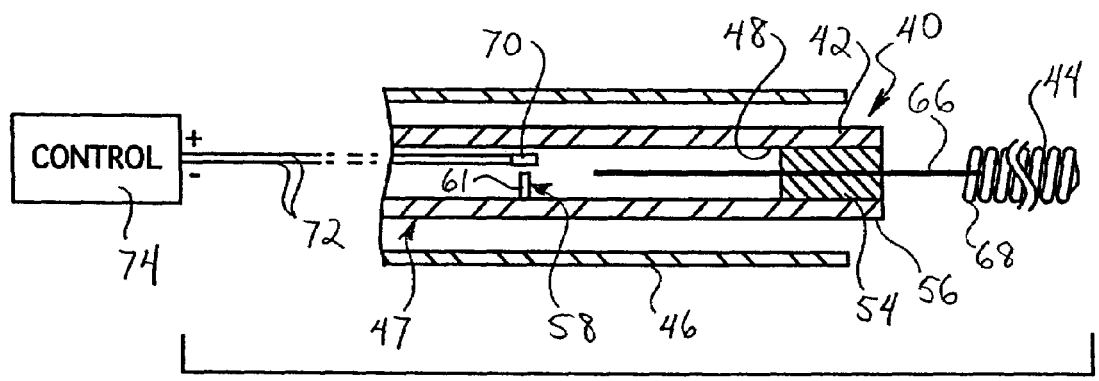
FIG. 5 is a side sectional view of the apparatus of FIG. 1, illustrating release of the therapeutic device.

In a first embodiment illustrated in FIGS. 1, 2 and 5, the pusher member has a portion 50 with an entry port 52 in communication with the interior lumen, and a plug 54 at the distal end 56 of the pusher member, typically secured within the distal end of the pusher member by adhesive, such as a cyanoacrylate adhesive, for example.

A first connector member 58 is mounted to the elongated, flexible pusher member, and has a severable portion 60 disposed within the elongated, flexible pusher member that is capable of being broken by heating. The first connector member is typically formed from a molded thermoplastic material, such as high density polyethylene. In the first embodiment, the first connector member may be molded in the form of a rod 61 extending across and connected between opposing sides of the interior diameter of the interior lumen of the pusher member, as is shown in FIGS. 1 and 2.

Figure 3:
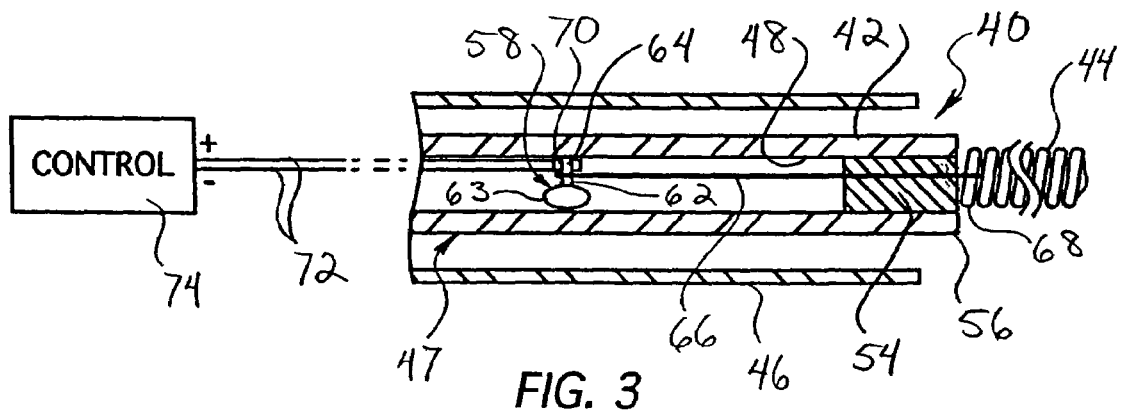
FIG. 3 is a top sectional view of a second embodiment of the apparatus for release and deployment of a therapeutic device.
Figure 6:
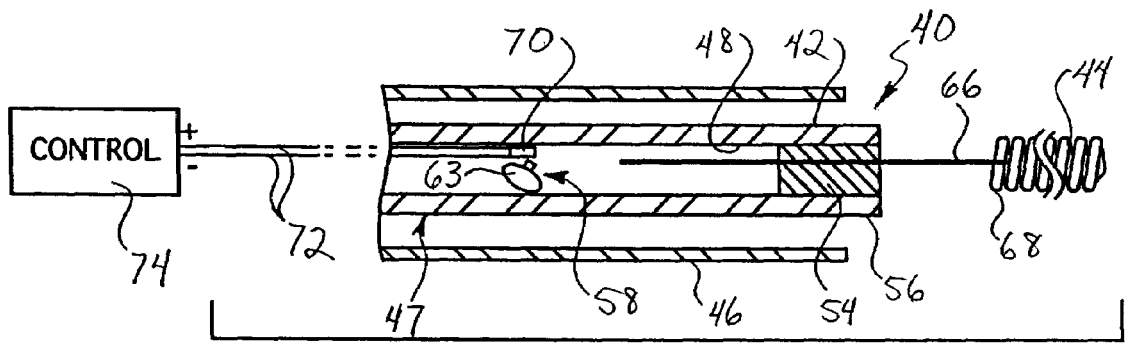
FIG. 6 is a side sectional view of the apparatus of FIG. 3, illustrating release of the therapeutic device.

In a second embodiment illustrated in FIGS. 3 and 6, in which the same elements from the first embodiment are shown with the same reference numbers, the first connector member may have the configuration of a post 62 connected at one end to the pusher member and having a free end with an enlarged portion 63 larger than the entry port, and having a severable portion 64 that is capable of being broken by heating, typically formed from a molded thermoplastic material, such as high density polyethylene, as is shown in FIG. 3.

Figure 4:
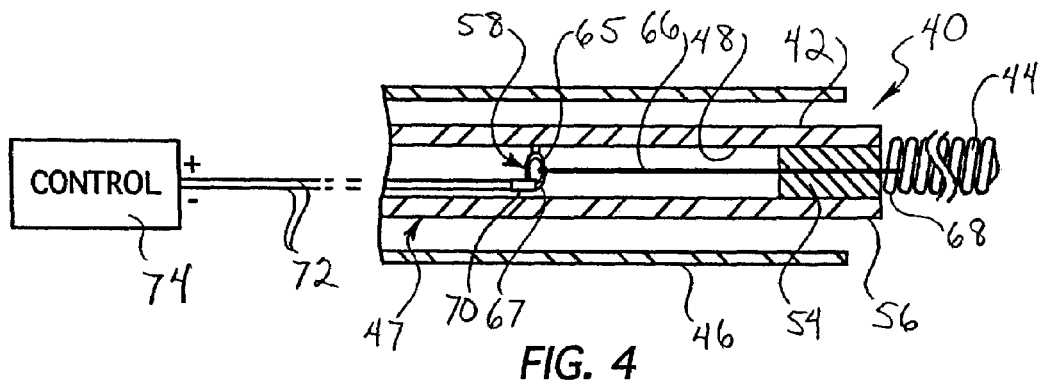
FIG. 4 is a top sectional view of a third embodiment of the apparatus for release and deployment of a therapeutic device.

In a third embodiment illustrated in FIGS. 4 and 7, in which the same elements from the first embodiment are shown with the same reference numbers, the first connector member may have the configuration of a ring 65 connected to the pusher member and having a severable portion 67, that is capable of being broken by heating, typically formed from a molded thermoplastic material, such as high density polyethylene, as is shown in FIG. 4, for example.

In each embodiment, the therapeutic device includes an elongated second connector member 66 connected to the therapeutic device, such as by being looped through an end coil 68 of a microcoil therapeutic device, for example. The elongated second connector member may alternatively be tied or bonded to the therapeutic device, such as by heat bonding, or by an adhesive such as a cyanoacrylate adhesive, for example. The elongated second connector member is typically looped around the first connector member when the first connector member is a rod or post, or through the first connector member, when the first connector member is a ring. The elongated second connector member may be a connector fiber, or a ribbon, that may be made of polyethylene, or another suitable fiber material, for example. In a presently preferred embodiment, the elongated second connector member is formed of polyethylene, and is typically about 0.015 to 0.030 inches in diameter, although the elongated second connector member can be as thin as about 0.0005 inches in diameter, and can be formed from a variety of thermoplastic materials with high tensile strength. The elongated second connector member may also optionally be formed of a suitable high tensile strength material, for example.

In the foregoing embodiments, a heat source such as a resistive heat source coil 70 is disposed in the interior lumen of the pusher member adjacent to the severable portion of the first connector member for heating the severable portion of the first connector member to cause the severable portion of the first connector member to break and release the elongated second connector member, to thereby detach and deploy the therapeutic device from the flexible pusher member when a desired placement of the therapeutic device within the vasculature is achieved. The heat source may be spaced apart from the distal end of the pusher member. The heat source is connected by electrical connectors 72 to a control unit 74 which supplies electrical current to the resistive heat source coil to cause the severable connector member to break and release the therapeutic device. Alternatively, the heat source may deliver heat to the severable connector member by other means, such as thermo-mechanical, electromagnetic or RF energy, for example. The lumen of the pusher member advantageously provides an insulative space and wall thickness to contain the heating of the severable connector member to avoid thermal damage to surrounding tissues, and to help contain pieces of the severable connector member that may be formed during heating of the severable connector member to deploy the therapeutic device. The therapeutic device is thus detachably connected to the first connector member by the elongated second connector member, for placement of the therapeutic device within the vasculature.

In a fourth embodiment illustrated in FIGS. 8-10, in which the same elements from the first embodiment are shown with the same reference numbers, the first connector member has the form of a ring 76 mounted to the elongated, flexible pusher member. In the fourth embodiment, the first connector member is preferably an induction ring providing a heat source disposed in the interior lumen of the pusher member, and having a narrow, thin edge portion or blade 78, that can be heated. The blade is positioned to be in contact with the elongated second connector member 66, such as a fiber or ribbon that will melt when heated sufficiently, as explained above. The second connector member is connected to the therapeutic device, so that when the blade of the induction ring is heated, such as by electrical current from electrical connectors 72 connected to a control unit 74, as explained above, the first connector member will sever the second connector member, to release the therapeutic device.

It will be apparent from the foregoing that while particular forms of the invention have been illustrated and described, various modifications can be made without departing from the spirit and scope of the invention. Accordingly, it is not intended that the invention be limited, except as by the appended claims.

The invention claimed is:

1. An apparatus for release and deployment of a therapeutic device within the vasculature of a patient, comprising:
   an elongated, flexible pusher member having an interior lumen;
   a first connector member mounted to said elongated, flexible pusher member;
   an elongated second connector member connected to a therapeutic device and detachably connected to the first connector member, said elongated second connector member thereby connecting the therapeutic device to the pusher member for placement of the therapeutic device within the vasculature, and said first connector member having a severable portion disposed within said elongated, flexible pusher member, the severable portion being capable of being broken by heating;
   a heat source disposed in the interior lumen of the pusher member adjacent to said severable portion of said first connector member for heating said severable portion of said first connector member to cause said severable portion of said first connector member to break and release the elongated second connector member for detaching and deploying the therapeutic device from the flexible pusher member when a desired placement of the therapeutic device within the vasculature is achieved.

2. The apparatus of claim 1, wherein said heat source comprises an electrical resistance heat source coil.

3. The apparatus of claim 1, further comprising a control unit, and wherein said heat source is connected by electrical connectors to the control unit which supplies electrical current to the heat source coil.

4. The apparatus of claim 1, wherein said flexible pusher member comprises a heat insulating shaft.

5. The apparatus of claim 1, wherein said first connector member is formed from a molded thermoplastic material.

6. The apparatus of claim 5, wherein said first connector member has the configuration of a rod extending across and connected between opposing sides of the interior diameter of the interior lumen of the pusher member.

7. The apparatus of claim 5, wherein said first connector member has the configuration of a post connected at one end to the pusher member and having a free end with an enlarged portion.

8. The apparatus of claim 5, wherein said first connector member has the configuration of a ring connected to the pusher member.

9. The apparatus of claim 5, wherein said thermoplastic is high density polyethylene.

10. The apparatus of claim 1, wherein said pusher member includes an entry port communicating with said interior lumen of said pusher member, and said heat source is disposed in the interior lumen of the pusher member adjacent to said entry port.

11. The apparatus of claim 1, wherein said elongated second connector member is a connector fiber.

12. The apparatus of claim 1, wherein said elongated second connector member comprises a ribbon.

13. The apparatus of claim 1, wherein said flexible pusher member has a distal tip, and the heat source is spaced apart from said distal tip of said flexible pusher member.

14. The apparatus of claim 1, wherein said therapeutic device is a vasoocclusive device.

15. The apparatus of claim 1, wherein said therapeutic device comprises a microcoil.

16. The apparatus of claim 1, wherein said heat source comprises an induction ring, and said first connector member includes said induction ring.

17. The apparatus of claim 16, wherein said induction ring has a blade portion that can be heated, said blade portion is positioned in contact with said elongated second connector member, and said elongated second connector member is severable by heating of said blade portion.

18. A method for release and deployment of a therapeutic device within the vasculature of a patient, the steps of the method comprising:

provic an elongated, flexible pusher member having an interior lumen;

providing a first connector member mounted to said elongated, flexible pusher member;

providing an elongated second connector member connected to a therapeutic device and detachably connected to the first connector member, said elongated second connector member thereby connecting the therapeutic device to the pusher member for placement of the therapeutic device within the vasculature, at least one of said first and second connector members having a severable portion disposed within said elongated, flexible pusher member, the severable portion being capable of being broken by heating;

positioning the therapeutic device at a desired placement within a patient's vasculature; and heating said severable portion within said interior lumen of said flexible pusher member to break said severable portion for detaching and deploying the therapeutic device from the flexible pusher member when a desired placement of the therapeutic device within a patient's vasculature is achieved.

19. The method of claim 18, wherein said first connector member includes said severable portion, and said step of heating said severable portion comprises disposing said severable portion of said first connector member adjacent to an electrical resistance heater disposed within said lumen of said flexible pusher member, and passing electrical current through said electrical resistance heater to break said severable portion of said first connector member.

20. The method of claim 18, wherein said second connector member includes said severable portion, and said first connector member includes an induction ring having a blade portion that can be heated by said induction ring, and said step of heating said severable portion comprises positioning said blade portion in contact with said elongated second connector member, and heating said blade portion to break said elongated second connector member.

21. The method of claim 18, wherein said therapeutic device is a vasoocclusive device.

22. The method of claim 18, wherein said therapeutic device comprises a microcoil.

* * * * *